(12) United States Patent  (10) Patent No.: US 8,926,518 B2
Culjat et al.  (45) Date of Patent: Jan. 6, 2015

(54) SCANNING DENTAL ULTRASONOGRAPHY PROBE

(75) Inventors: Martin Culjat, Los Angeles, CA (US);
Rahul Singh, Palo Alto, CA (US); Mijin Choi, Jersey City, NJ (US); Shane White, Los Angeles, CA (US)

(73) Assignee: Farus, LLC, Vista, CA (US)

( * ) Notice: Subject to any disclaimer, the term of this patent is extended or adjusted under 35 U.S.C. 154(b) by 219 days.

(21) Appl. No.: 13/224,729

(22) Filed: Sep. 2, 2011

(65) Prior Publication Data
US 2013/0060144 A1 Mar. 7, 2013

(51) Int. Cl.
*A61B 8/14* (2006.01)
*A61B 8/08* (2006.01)
*A61B 8/12* (2006.01)
*A61B 17/16* (2006.01)

(52) U.S. Cl.
CPC ............ *A61B 8/14* (2013.01); *A61B 8/0875* (2013.01); *A61B 8/12* (2013.01); *A61B 17/1642* (2013.01); *A61B 17/1697* (2013.01)
USPC ............ 600/459; 600/437; 600/443; 600/463

(58) Field of Classification Search
CPC .......... A61C 1/107; A61C 19/04; A61B 8/12; A61B 17/1642; A61B 17/1697; A61B 17/320068
USPC ............ 600/437, 443, 459, 463; 433/25, 215
See application file for complete search history.

(56) References Cited

U.S. PATENT DOCUMENTS

| | | | |
|---|---|---|---|
| 4,637,256 A | 1/1987 | Sugiyama et al. | |
| 5,680,863 A | 10/1997 | Hossack | |
| 5,957,850 A | 9/1999 | Marian, Jr. | |
| 8,221,323 B2 * | 7/2012 | Zhang et al. | 600/437 |
| 2002/0193798 A1 * | 12/2002 | Oh et al. | 606/80 |
| 2007/0078345 A1 | 4/2007 | Mo | |
| 2007/0276254 A1 | 11/2007 | Yang | |
| 2009/0306506 A1 * | 12/2009 | Heger et al. | 600/443 |
| 2010/0191123 A1 * | 7/2010 | Tsung | 600/463 |
| 2010/0227295 A1 * | 9/2010 | Maev et al. | 433/215 |
| 2012/0244489 A1 * | 9/2012 | Carnahan | 433/25 |

OTHER PUBLICATIONS

Ghorayeb, et al.; Ultrasonography in Dentistry; IEEE Transactions on Ultrasonics, Ferroelectrics, and Frequency Control; vol. 55, No. 6; Jun. 2008; pp. 1256-1266.
Culjat, Ph.D., et al.; Ultrasound Detection of Submerged Dental Implants Through Soft Tissue in a Porcine Model; Journal of Prosthetic Dentistry; vol. 99, Iss. 3; 2008; pp. 218-224.
International Searching Authority; International Search Report and Written Opinion; Application No. PCT/US12/51875; Nov. 2, 2012; 9 pages.

\* cited by examiner

*Primary Examiner* — Baisakhi Roy
(74) *Attorney, Agent, or Firm* — File-EE-Patents.com; Jay A. Chesavage (57) ABSTRACT

A dental ultrasonography probe includes a probe tip having a scanning ultrasonography transducer that generates a narrow beam ultrasonic transmission signal over a sequence of beam angles, that receives an ultrasonic return signal, and that generates an ultrasonic receive signal in response to the ultrasonic return signal to identify and measure dental and craniofacial objects and features. A probe body has a longitudinal axis that is substantially perpendicular to a longitudinal axis of the probe tip.

20 Claims, 12 Drawing Sheets

SCANNING DENTAL ULTRASONOGRAPHY PROBE

STATEMENT REGARDING FEDERALLY SPONSORED RESEARCH OR DEVELOPMENT

Portions of the present invention were funded by the National Institutes of Health (NIH), National Institute of Dental and Craniofacial Research (NIDCR) NIH/NIDCR Award #1R43DE021326-01.

CROSS REFERENCE TO RELATED PATENTS

NOT APPLICABLE

INCORPORATION-BY-REFERENCE OF MATERIAL SUBMITTED ON A COMPACT DISC

NOT APPLICABLE

BACKGROUND OF THE INVENTION

1. Technical Field of the Invention

This invention relates generally to sensors for monitoring atrial fibrillation in a patient.

2. Description of Related Art

Various dental procedures require the dentist or oral surgeon to precisely locate a patient's existing dental implants and pre-implants, to assess soft tissue thickness and to assess or locate other features in the jaw. For example, during dental implant surgery, direct knowledge of the soft tissues and bony structures in the mouth can aid the surgeon in placing the implant by optimizing positioning of the implant to structurally sound regions, with appropriate soft tissue management, avoid existing implants and further to avoid nerves within the jaw.

The most common technique currently used to generate this information is to use a rigid periodontal probe. However, a rigid probe can be inaccurate and invasive. Conventional dental X-ray's can also be used for these purposes. However, conventional X-rays do not provide depth information required for true location or depth assessment. X-ray computed tomography (CT) can be employed, however, this technique is often not practical due to cost, cannot be performed in real time, intra-operatively during a surgical manipulation, and uses ionizing radiation.

Further disadvantages of conventional approaches will be evident to one skilled in the art when presented the disclosure that follows.

BRIEF SUMMARY OF THE INVENTION

The present invention is directed to apparatus and methods of operation that are further described in the following Brief Description of the Drawings, the Detailed Description of the Invention, and the claims. The features and advantages of the present invention will become apparent from the following detailed description of the invention made with reference to the accompanying drawings.

DETAILED DESCRIPTION OF THE INVENTION

Figure 1:
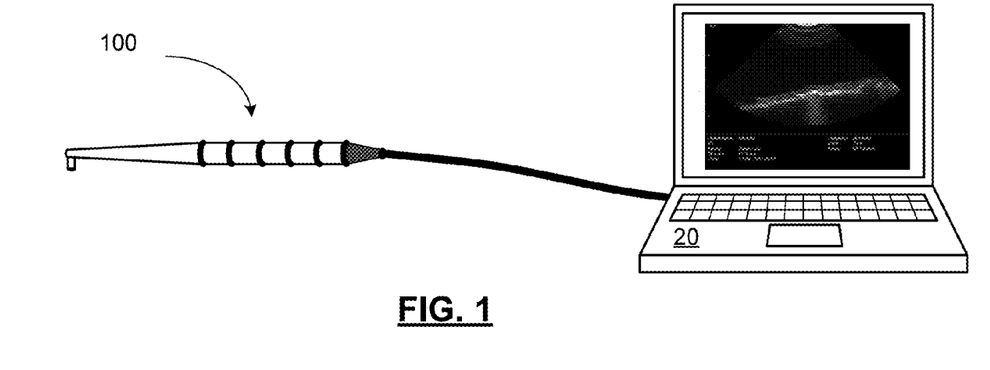
FIG. 1 is a block diagram representation of an embodiment of dental ultrasonography system including dental ultrasonography probe 100 and personal computer 20 in accordance with the present invention.

FIG. 1 is a block diagram representation of an embodiment of dental ultrasonography system including dental ultrasonography probe 100 and personal computer 20 in accordance with the present invention. The dental ultrasonography probe 100 includes an ultrasonic transducer such as an ultrasound sector scanning transducer or ultrasound array for imaging of the human jaw through the gums and a processing and display device such as personal computer 20 for processing signals from the transducer and displaying the images produced therefrom. While the processing and display device is shown as a personal computer 20, in an alternative, the dental ultrasonography probe 100 can be mated to an existing dental workstation, or implemented in conjunction with a computing device with another portable display such as a tablet, phone, personal digital assistant, etc.

The dental ultrasonography probe 100 focuses on detection or imaging of structures in the mouth, including, but not limited to dental implants, the mental foramen, dehiscences, other bony defects and contours, as well as soft tissue thickness measurements. Ultrasonography is ideally suited for this application, because: (a) it can be used in real-time before or during surgeries, treatment planning or checkups; (b) data is directly located to the exact site being imaged on the patient, as directly viewed by the dentist or oral surgeon; (c) it is non-invasive and without ionizing radiation; and (d) it can be performed with an inexpensive and portable instrument by a dentist, surgeon, assistant, or technician.

As shown, the dental ultrasonography probe 100 is thin and has a tip that extends into mouth like a dental instrument. The dental ultrasonography probe produces an ultrasound beam by coupling against the soft tissue, using saliva, water, gel, gel pad, or another couplant. The ultrasonic bean penetrates through the gingiva to detect dental implants, dehiscences, and mental foramina, and generates sector scan images of the jaw that are displayed in the personal computer 20. In this fashion, the system can be used for preoperative measurement of soft tissue thickness, precise location of buried healing implants and precise measurement of overlying tissue thickness, identification of surface bony features such as foramina; and identification of bony defects or fenestrations. Therefore it can be used to guide dental implant procedures and other procedures in the mouth.

Further details regarding the operation of the dental ultrasonography system will be described in greater detail in conjunction with FIGS. 2-30, which further describe several optional functions and features.

Figure 2:
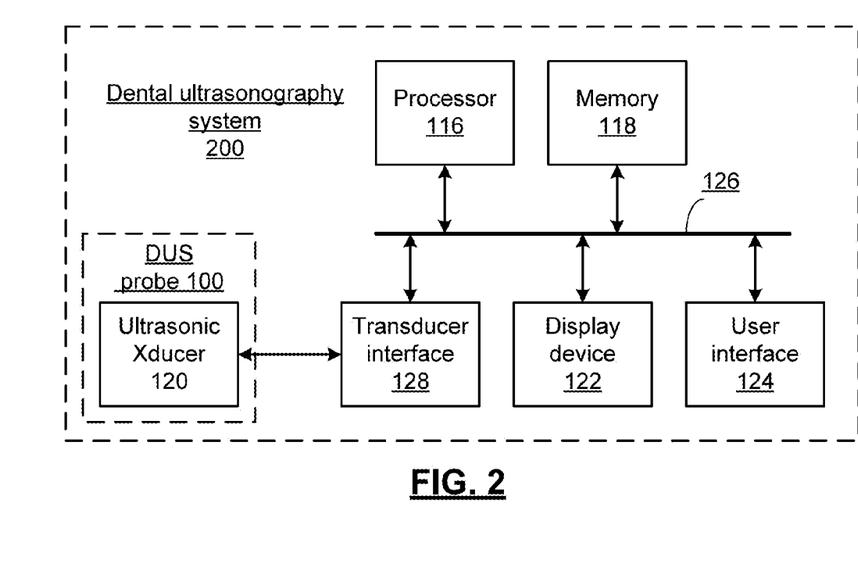
FIG. 2 is a block diagram representation of an embodiment of dental ultrasonography system 200 in accordance with the present invention.

FIG. 2 is a block diagram representation of an embodiment of dental ultrasonography system 200 in accordance with the present invention. In particular, dental ultrasonography system 200 includes processor, 116, memory 118, dental ultrasonography probe 100 that includes ultrasonic transducer 120, transducer interface 128, display device 122 and user interface 124 that are coupled via bus 126. While a particular bus architecture is shown that includes bus 126, other architectures with additional direct connectivity between modules or with additional buses, wired or wireless, are likewise possible.

As discussed in conjunction with FIG. 1, the ultrasonic transducer 120 includes an ultrasound sector scanning transducer, ultrasonic array or other ultrasonic transducer for imaging of the human jaw through the gums and in particular for detection or imaging of structures in or near the mouth. This imaging includes but is not limited to the imaging and/or automatic detection of dental implants, the mental foramen, dehiscences, other bony defects and contours. The imaging further includes soft tissue thickness measurements such as measurements of the thickness of gum tissue, lips, cheeks and other soft tissues in or near the mouth. In an embodiment of the present invention, the processor, 116, memory 118, transducer interface 128, display device 122, user interface 124 and bus 126 are implemented via a computer such as personal computer 20, however other computers or processing devices can likewise be employed.

Transducer interface 128 includes one or more drivers for generating transducer signaling that causes the ultrasonic transducer 120 to produce a narrow beam ultrasonic transmission signal over a sequence of beam angles. In an embodiment of the present invention, the ultrasonic transducer 120 includes a piezoelectric transducer that produces ultrasonic waves, such as in the range of 1 MHz to 30 MHz. These ultrasonic waves travel through the gum tissue in the mouth and are partially reflected by structures under the gum line to produce echo returns. The ultrasonic transducer 120 generates an ultrasonic receive signal in response to the ultrasonic echo return signal. The ultrasonic receive signal is amplified, sampled and converted to digital data by the transducer interface 128 for processing by processor 116 in conjunction with corresponding beam angle data. In particular, the time it takes for an echo return to be received from the time it was transmitted indicates the depth of the structure that produced the echo. In addition, the strength of the echo can indicate the density of the structure that produced the echo. The transducer interface can further include a wireless interface such as a Bluetooth interface, 802.11 interface, wireless medical telemetry service (WMTS) interface or other wireless connection or a wired interface such as a universal serial bus (USB) interface, Firewire interface, or other serial or parallel interface for coupling to the dental ultrasonography probe 100. While shown as a separate device, portions of the transducer interface 128 can be incorporated in the dental ultrasonography probe 100 itself.

Processor 116 can be implemented using a shared processing device, individual processing devices, or a plurality of processing devices that operate in conjunction with memory 118. Such a processing device may be a microprocessor, micro-controller, digital signal processor, microcomputer, central processing unit, field programmable gate array, programmable logic device, state machine, logic circuitry, digital circuitry, and/or any device that manipulates signals based on operational instructions. The memory 118 may be a single memory device or a plurality of memory devices. Such a memory device may be a read-only memory, random access memory, volatile memory, non-volatile memory, static memory, dynamic memory, flash memory, and/or any device that stores digital information. Note that when the processor 116 implements one or more of its functions via a state machine, digital circuitry, and/or logic circuitry, the memory storing the corresponding operational instructions is embedded with the circuitry comprising the state machine, digital circuitry, and/or logic circuitry.

In an embodiment of the present invention, the memory 118 stores an application such as an ultrasonography application that is executed by the processor 116. User interface 222 includes user input devices such as a touch screen, one or more buttons, speakers and/or other user interface devices to be used, in conjunction with display device 122 to receive user input and to provide output to the user in order to control the operation of the ultrasonography application. In operation, the ultrasonography application analyzes the ultrasonic receive data in conjunction with corresponding beam angle data to produce ultrasound images for display on the display device 122. Display device 122 can include a liquid crystal display, a light emitting diode display, a plasma display, a projection display or other display device.

In addition, the memory 118 can store a plurality of templates, such as exemplars of various structures to be detected such as soft tissues, dental implants, unerupted teeth, fixation screws, or other metallic objects, the mental foramen, dehiscences or fenestrations over teeth or implants, inherited defects to the craniofacial bones, such as a cleft palate or other defects, acquired defects, such as a gunshot or other traumatic damage are to the craniofacial bones, stones, in salivary ducts or glands, and other bony defects in the region of the teeth, jaw, checks, lips or other areas in or near the mouth.

The ultrasonography application can include a pattern recognition algorithm that compares the ultrasonic receive data and/or ultrasonic image data to the exemplars. In particular, the pattern recognition algorithm operates to automatically detect, identify, locate and/or measure soft tissues, dental implants, the mental foramen, dehiscences, and other bony defects in the ultrasonic images when the ultrasonic receive data and/or ultrasonic image data include a corresponding one of the plurality of exemplars. In response, different colors, text, graphical elements or other indicators can be used to display, in real time, different structures that have been automatically identified, detected and/or located to aid the user in visualizing the placement, size, shape and orientation of these structures in the patient's mouth during dental diagnosis and therapy and optionally to further to aid in the manual measurement these structures.

Figure 3:
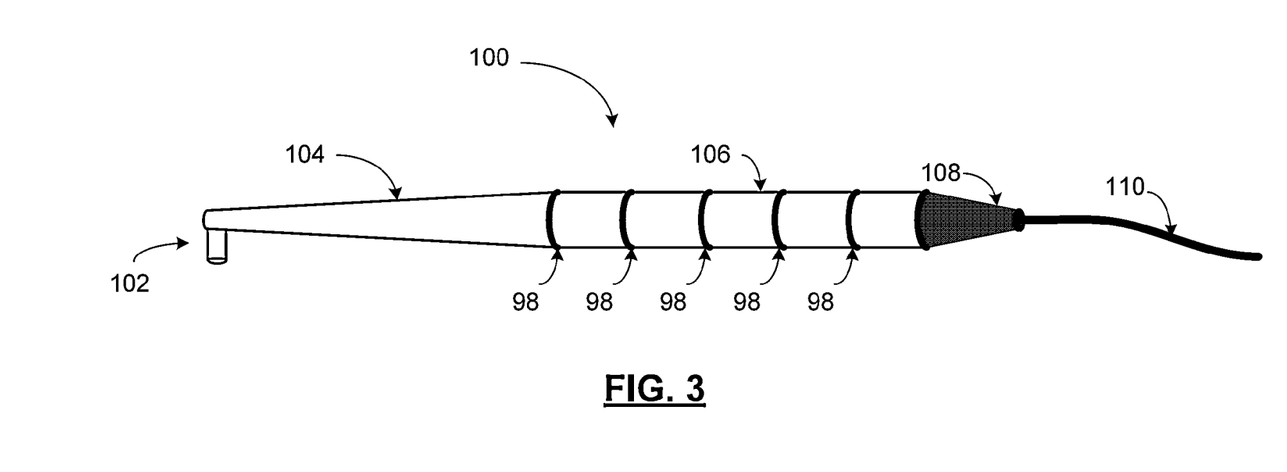
FIG. 3 is a side view of dental ultrasonography probe 100 in accordance with the present invention.

FIG. 3 is a side view of dental ultrasonography probe 100 in accordance with the present invention. In particular, dental ultrasonography probe 100 includes a probe tip 102 having a scanning ultrasonography transducer, such as ultrasonography transducer 120 that generates a narrow beam ultrasonic transmission signal over a sequence of beam angles, that receives an ultrasonic return signal, and that generates an ultrasonic receive signal in response to the ultrasonic return signal. The probe body includes a tapered end 104 and a substantially cylindrical portion 106 having a plurality of annular gripping elements 98 such as rubber or silicon rings or other grippers to aid a user in securely gripping the dental ultrasonography probe 100 in the user's hand. At the opposing end of the probe body, a flexible tapered gasket 108, such as a rubber gasket or other gasket is coupled to the probe body for enclosing the wiring 110 from the scanning ultrasonography transducer. While not specifically shown, a disposable sterile condom can be deployed over the probe tip 102 for enhanced sterility.

Figure 4:
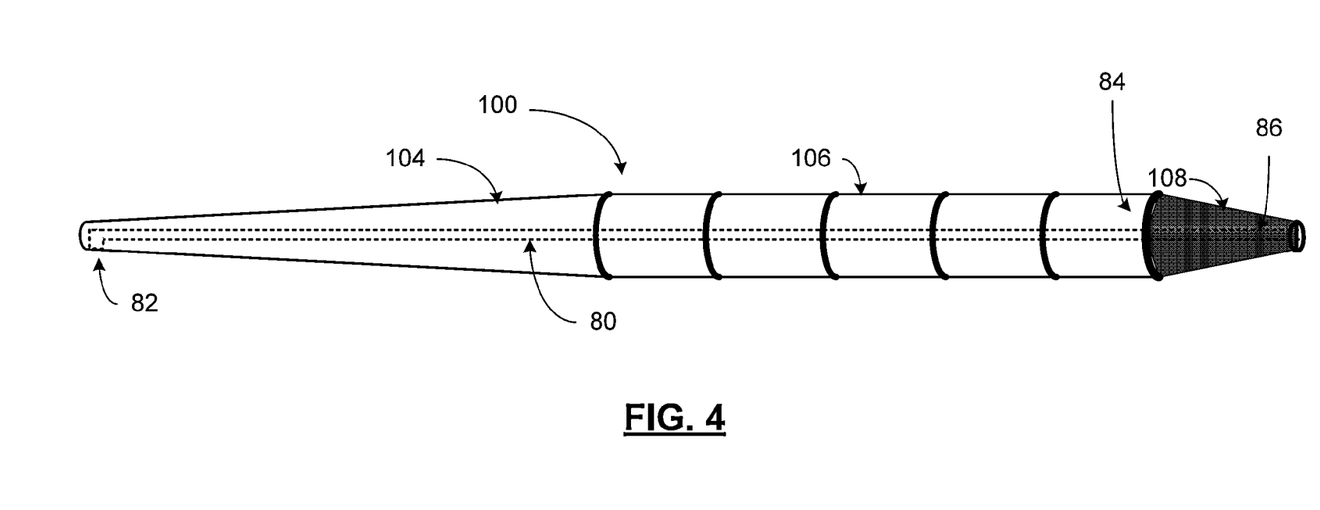
FIG. 4 is a side view of an embodiment of a probe body of a dental ultrasonography probe 100 in accordance with the present invention.

FIG. 4 is a side view of an embodiment of a probe body of a dental ultrasonography probe 100 in accordance with the present invention. The probe body includes an inner cavity 80 having an opening 82 at the tapered end 104 and an opening 84 at that opposing end for enclosing wiring from the scanning ultrasonography transducer. The flexible tapered gasket 108 is coupled to the probe body at the second opening 84. The flexible tapered gasket 108 includes an inner cavity 86 for enclosing the wiring 110 from the scanning ultrasonography transducer.

Figure 5:
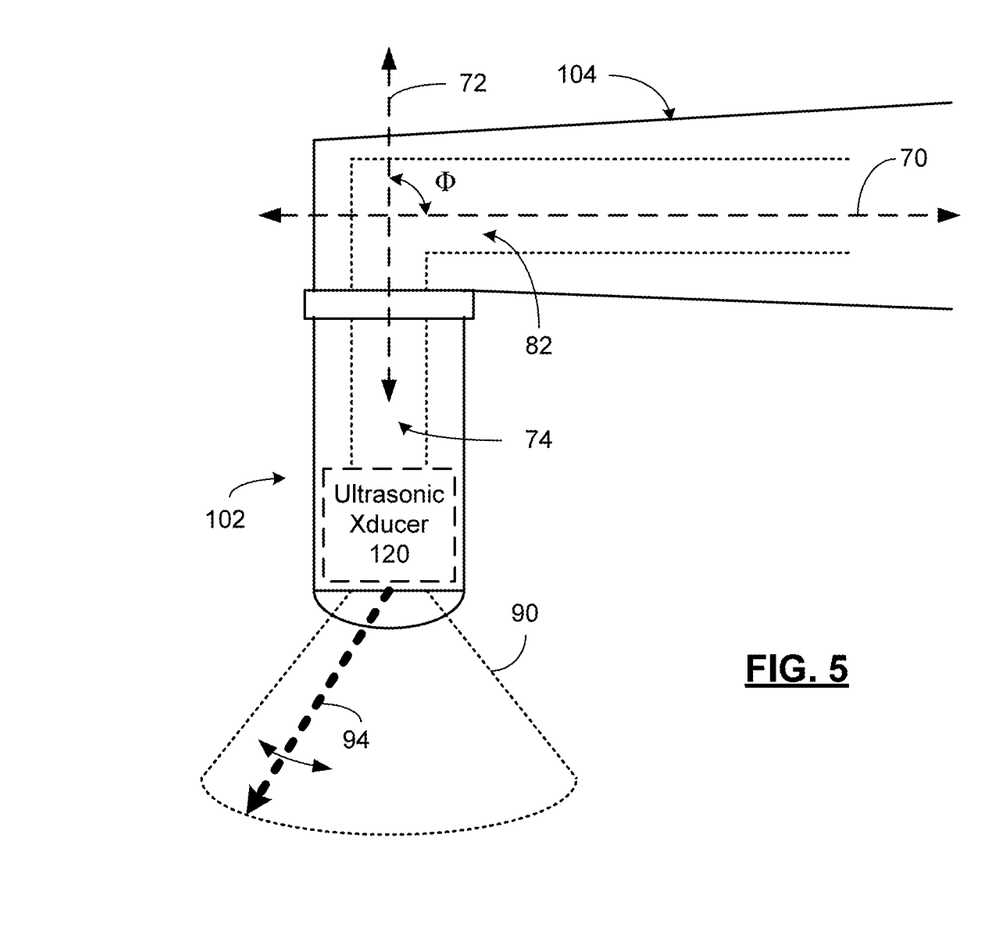
FIG. 5 is a side view of an embodiment of a probe tip 102 in accordance with the present invention.

FIG. 5 is a side view of an embodiment of a probe tip 102 in accordance with the present invention. As shown, the probe tip 102 includes an inner cavity 74 that mates with the inner cavity 82 at the tapered end 104 of the probe body. The probe body has a longitudinal axis 70 that is substantially perpendicular to a longitudinal axis 72 of the probe tip 102. In particular, the longitudinal axis 70 forms an angle Φ with the longitudinal axis 72 of the probe tip 102, where Φ=90°+/−20°, however other configurations are likewise possible.

The probe tip 102 includes an ultrasonic transducer 120. The ultrasonic transducer 120 can be a scanning ultrasonography transducer having a piezoelectric element that produces a narrow beam 94 that is mechanically rotated at a sequence of beam angles to produce a two-dimensional sector image. In particular, the piezoelectric element rotates partially within a probe tip 102 to forms an image with a pie-shaped field of view 90 that corresponds to the angle of rotation. A single scan line is obtained at each angle by sending a pulse and receiving the reflected information from different depths at that angle. Scan lines are taken at each angle of a sequence of angles, and a two-dimensional image is reconstructed by the processor 116 by combining the scan lines together. The number of scan lines depends on the sampling rate of the scanner. In the alternative, a phased ultrasound array, linear ultrasound array, annular ultrasound array, two-dimensional array, mechanically rotating array, or other ultrasound device that can provide two-dimensional or three dimensional imagery can be employed to provide similar imaging. Ultrasound transducers using piezoelectric materials, including crystals, single-crystal, ceramics, piezoelectric composites, sol-gels, or polymers may be used, or capacitive micromachined ultrasound transducers (CMUTs) or other materials may be used.

Whether implemented via a scanning ultrasonography transducer or an ultrasonic array, a wider viewing angle can be implemented up to and including 360 degrees. Further, three dimensional scanning, rather than two dimensional scanning, can likewise be employed based on the configuration of the ultrasonic transducer and the tip. In particular, the scanning element can be rotated or translated along one or more other degrees of freedom to create a 3D volumetric image. In a particular embodiment, the rotating element is also translated up or down the shaft to encompass an additional degree of motion. The 2D images at each sampling point along the shaft can be used to reconstruct a 3D image.

It should be noted that the user can be given the option to select a particular portion of the image for viewing. In this fashion, a user could select a "sector" from this image, such as a 60-90 degree slice of the image in two or three dimensions for detection and display. Further, while the imaging could be performed over a range of anywhere from 0-360 degrees, the image could display a null region, such as all black, where there is no contact with tissues.

Figure 6:
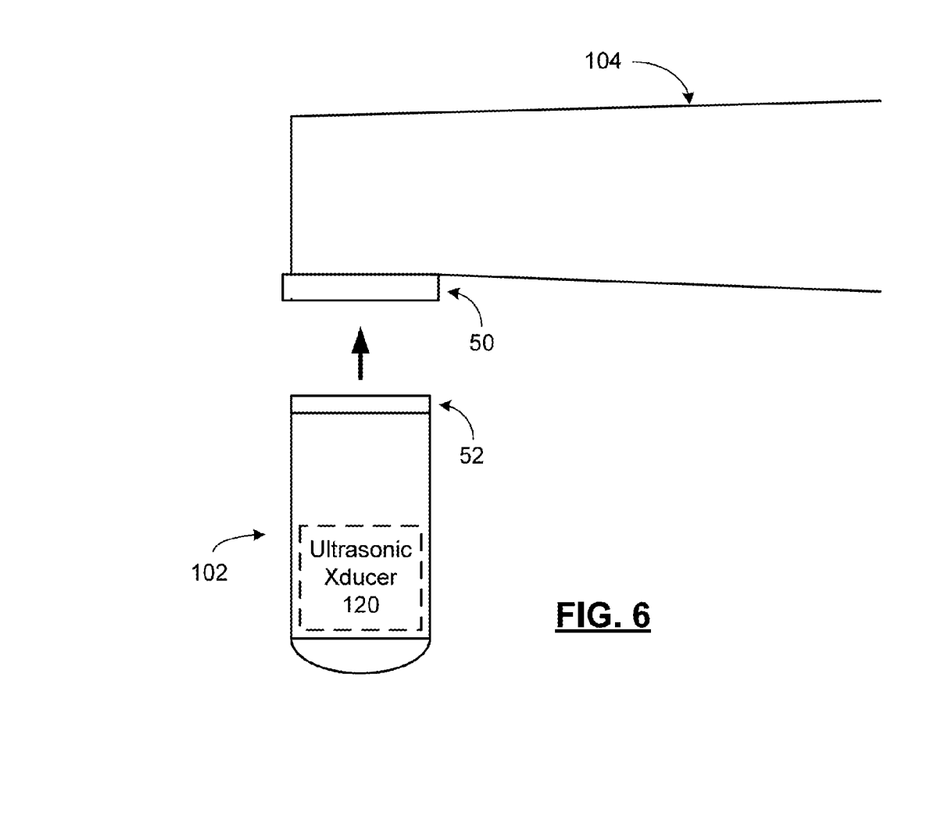
FIG. 6 is a side view of an embodiment of a probe tip 102 in accordance with the present invention.

FIG. 6 is a side view of an embodiment of a probe tip 102 in accordance with the present invention. In this embodiment the probe tip 102 is interchangeably connected to the probe body 104 via plug 52 and jack 50 that provide a mechanical coupling 120. In one embodiment, the probe tip 102 includes a plastic/rubber lens that couples to a fluid or gel in the inner cavity to couple ultrasonic transmit and receive signals through the tip to the mouth of the patient. In another embodiment, a larger portion of the probe that includes the probe tip, such as probe tip 102, is replaceable. In this fashion, an entire probe head can be interchangeably connected via a similar mechanical coupling.

This removable nature of the probe tip 102 or probe head provides several advantages. The probe tip 102 can be removed for cleaning and sterilization or can be disposable for improved sterility. Probe tips 102 of different shapes and potentially with different viewing angles in two or three dimensions (such as fan or arc shaped, bulb-shaped, pyramid-shaped, cone shaped, cylindrical shaped, donut shaped, etc.) can be selectively attached to fit the needs of different patients and different applications. Further probe tips 102 of different sizes can be employed. In addition, the plug 52 and jack 50 can permit the probe tip 102 to be rotatable over 360 degrees to a selected one of a plurality of scan axes. In the alternative, the probe tip 102 can be selectable from a plurality of probe tips with a corresponding plurality of fixed scan axes.

It should also be noted that a probe tip cover (not expressly shown) could be used in addition to or in lieu of a replaceable probe tip. The probe tip cover, such as a "condom" or a more rigid equivalent (i.e., silicone or hard plastic), can slide over or snap over a larger portion of the probe. One purpose of this cover is to have a disposable part that spans the whole mouth, or a portion thereof, so that sterilization of all or part of the probe would not be needed. The condom or more rigid part can incorporate coupling liquid or gel so as to maintain the acoustic path. In the implementation where probe tip 102 is disposable, the probe tip 102 could also have a plastic bag attached to it (or attachable to it) that serves as a sleeve over the shaft of the tool.

Figures 7, 8, 9:
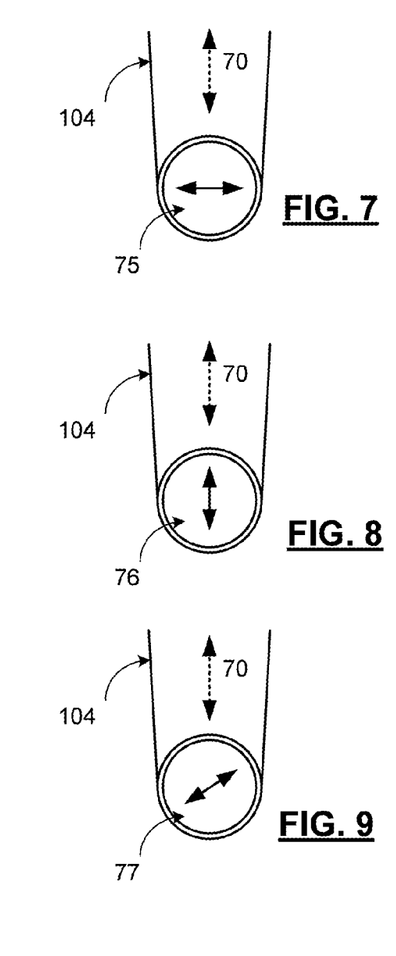
FIG. 7 is a bottom view of an embodiment of a probe tip 75 in accordance with the present invention.
FIG. 8 is a bottom view of an embodiment of a probe tip 76 in accordance with the present invention.
FIG. 9 is a bottom view of an embodiment of a probe tip 77 in accordance with the present invention.

FIGS. 7-9 present a bottom view of embodiments of probe tips 75, 76 and 77 in accordance with the present invention. As discussed in conjunction with FIG. 6, the probe tip can be selectable from a plurality of probe tips with a corresponding plurality of fixed scan axes. Probe tips 75, 76 and 77 present three such probe tips. While each of the probe tips 75, 76 and 77 have a circular cross section, other shapes can be employed as discussed in conjunction with FIG. 6.

As shown, each of the probe tips 75, 76 and 77 have an arrow graphic that is etched, printed or otherwise applied to the base of the tip to indicate the scan axis of the probe tip. Probe tip 75 has a scan axis the produces a two-dimensional sector scan that is perpendicular to the longitudinal axis 70 of the tapered end 104 of the probe body. Probe tip 76 has a scan axis the produces a two-dimensional sector scan that is parallel to the longitudinal axis 70 of the tapered end 104 of the probe body. Probe tip 77 has a scan axis the produces a two-dimensional sector scan that is at another angle, such as 45 degrees to the longitudinal axis 70 of the tapered end 104 of the probe body.

While represented as three separate probe tips 75, 76 and 77, as noted in conjunction with FIG. 6 a single rotatable probe tip 102 could implement each of these three scan axes shown in FIGS. 7-9. Further, such as probe tip 102 could include a similar scan axis arrow graphic to indicate to the user the scan axis for rotation to the desired angle.

Figure 10:
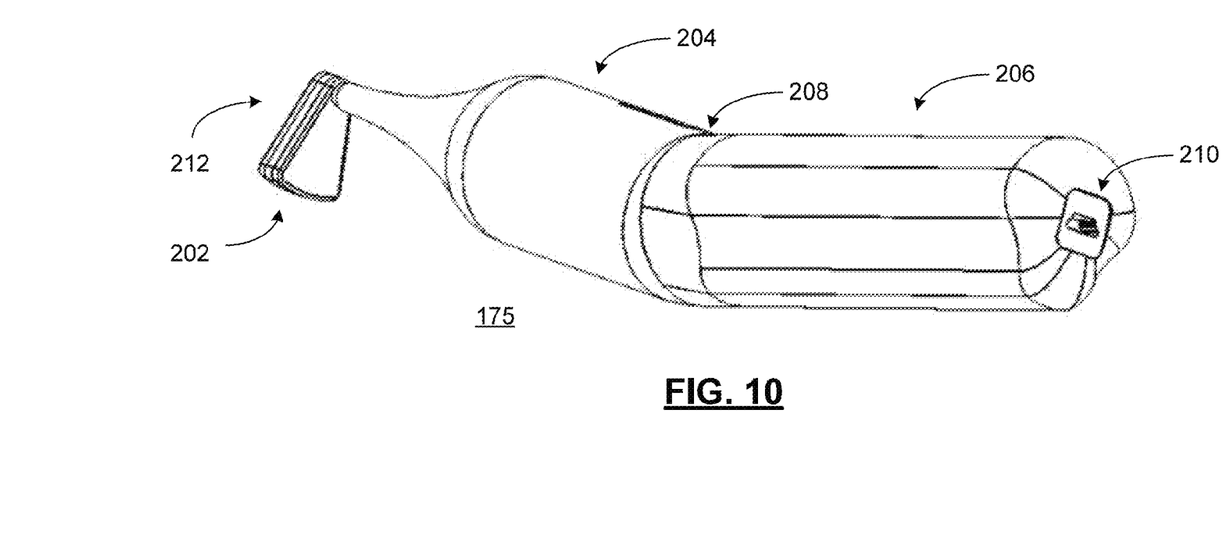
FIG. 10 is a side view of an embodiment of a dental ultrasonography probe 175 in accordance with the present invention.

FIG. 10 is a side view of an embodiment of a dental ultrasonography probe 175 in accordance with the present invention. In particular, dental ultrasonography probe 175 is another embodiment of dental ultrasonography probe 100 described in conjunction with FIGS. 1-9 and used in conjunction with a dental ultrasonography system, such as dental ultrasonography system 200. In this embodiment, the dental ultrasonography probe 200 includes a substantially cylindrical body 208 having body portions 204 and 206 that are coupled via a joint with a slight bend. The body portion 206 has two recessed sides that, in conjunction with the bend between body portions 204 and 206, make the device easier to hold in the hand of the user. While not expressly shown the recessed sides and/or other portions of the substantially cylindrical body 208 can be covered with rubber, silicon or other non-skid surface to form one or more gripping elements to aid the user in securely gripping the dental ultrasonography probe 175.

The probe tip 212 functions as probe tip 102 but has a fan shape with a convex surface 202. The probe end includes a connector, such as the min-USB connector shown for coupling the dental ultrasonography probe 200 to a processing display device, such as personal computer 20 or other device. In an embodiment of the present invention, a gasket is provided for water sealing the USB connection or otherwise providing additional water resistance due to the dental environment of the probe.

Figure 11:
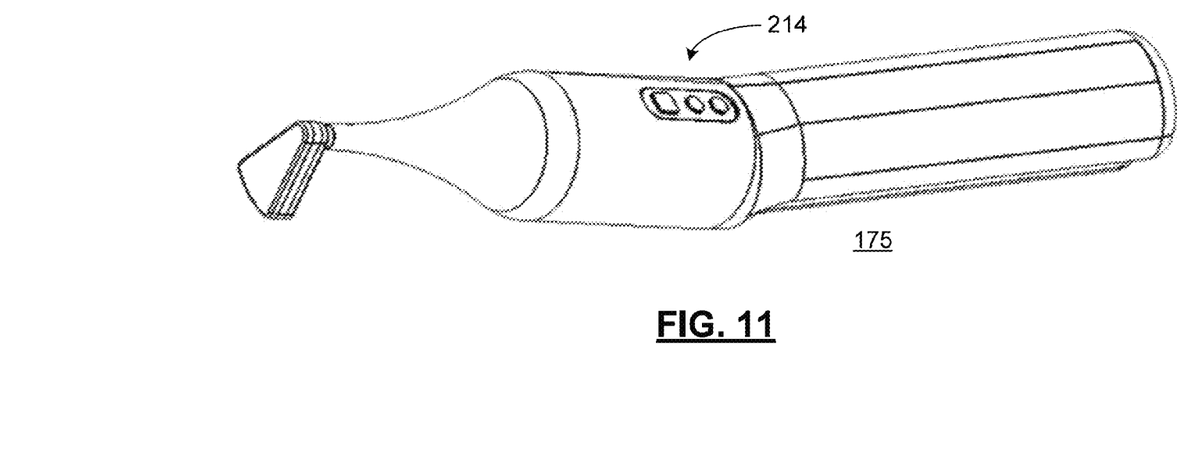
FIG. 11 is a top view of an embodiment of a dental ultrasonography probe 175 in accordance with the present invention.

FIG. 11 is a top view of an embodiment of a dental ultrasonography probe 175 in accordance with the present invention. As shown, dental ultrasonography probe 175 includes a plurality of user interface devices, such as buttons 214, for enabling the user to turn the dental ultrasonography probe 175 on and off or otherwise to engage one or more other functions of the dental ultrasonography system 200.

Figure 12:
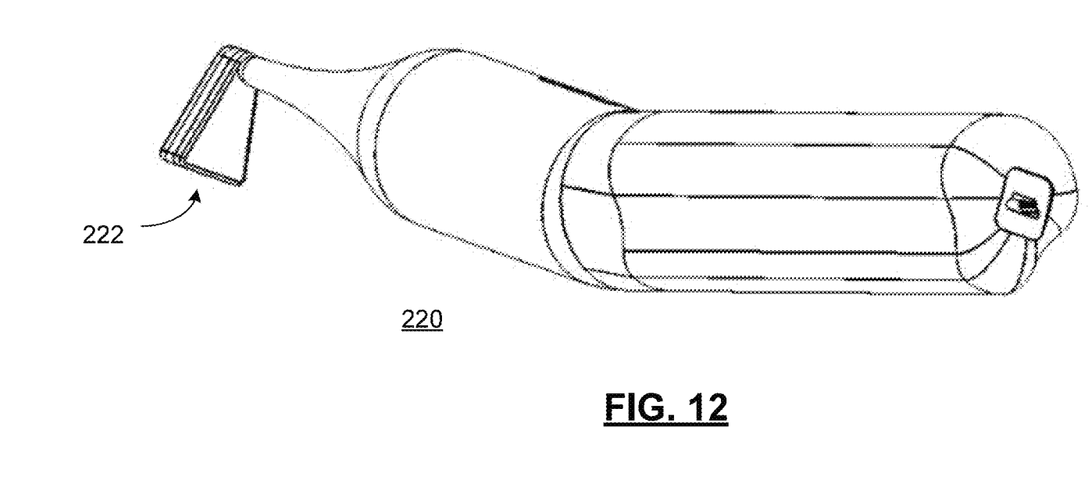
FIG. 12 is a side view of an embodiment of a dental ultrasonography probe 220 in accordance with the present invention.

FIG. 12 is a side view of an embodiment of a dental ultrasonography probe 220 in accordance with the present invention. In particular, dental ultrasonography probe 220 is another embodiment of dental ultrasonography probe 100 described in conjunction with FIGS. 1-9 and used in conjunction with a dental ultrasonography system, such as dental ultrasonography system 200. Dental ultrasonography probe 220 is similar to dental ultrasonography probe 175, yet with a flat tip surface 222.

Figure 13:
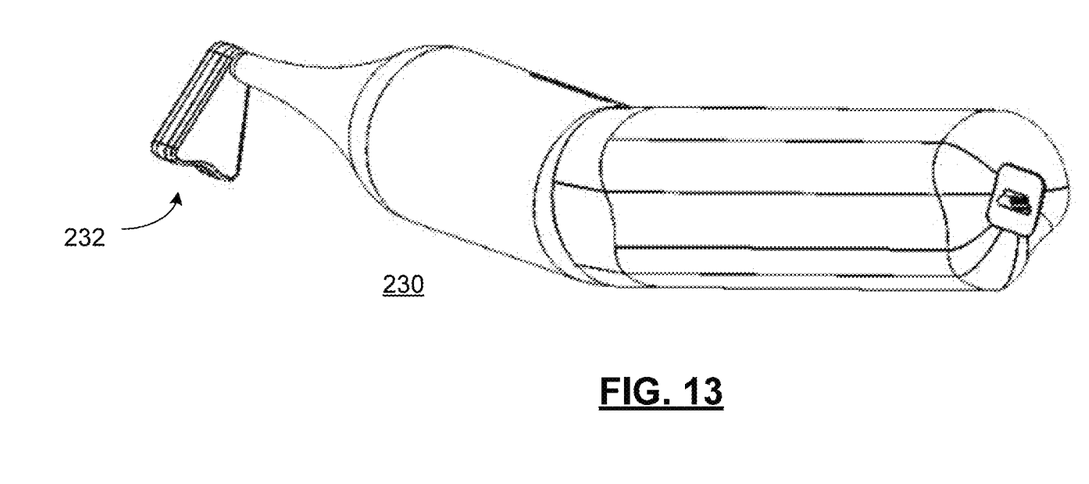
FIG. 13 is a side view of an embodiment of a dental ultrasonography probe 230 in accordance with the present invention.

FIG. 13 is a side view of an embodiment of a dental ultrasonography probe 230 in accordance with the present invention. In particular, dental ultrasonography probe 230 is another embodiment of dental ultrasonography probe 100 described in conjunction with FIGS. 1-9 and used in conjunction with a dental ultrasonography system, such as dental ultrasonography system 200. Dental ultrasonography probe 230 is similar to dental ultrasonography probe 175, yet with a concave surface 232.

Figure 14:
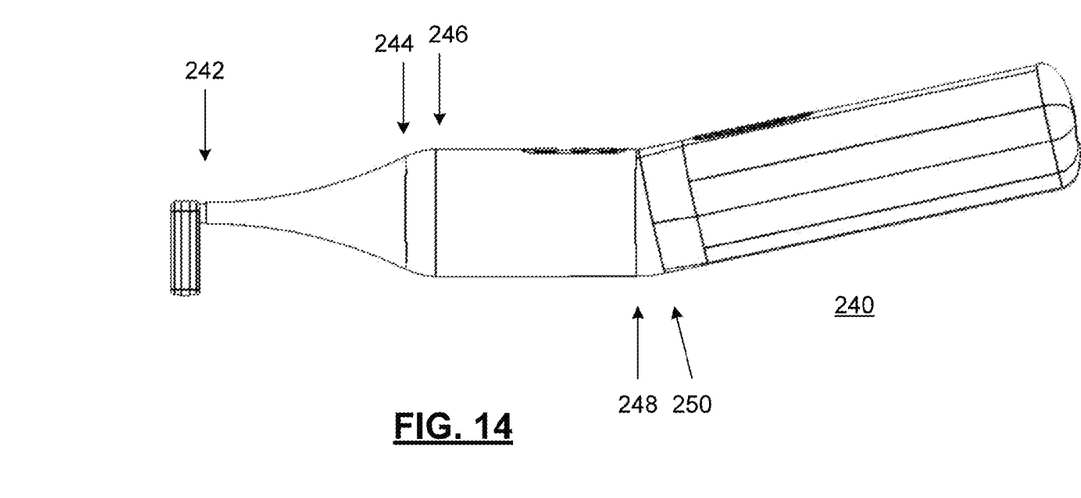
FIG. 14 is a side view of an embodiment of a dental ultrasonography probe 240 in accordance with the present invention.

FIG. 14 is a side view of an embodiment of a dental ultrasonography probe 240 in accordance with the present invention. In particular, dental ultrasonography probe 230 is another embodiment of dental ultrasonography probe 100 described in conjunction with FIGS. 1-9 and used in conjunction with a dental ultrasonography system, such as dental ultrasonography system 200. Dental ultrasonography probe 230 is similar to dental ultrasonography probe 175, yet includes one or more rotating joints 242, 244, 246, 248 and 250 allowing portions of the probe and probe tip to rotate with respect to one another to provide greater flexibility in the positioning and orientation of the probe and the probe tip.

Figure 15:
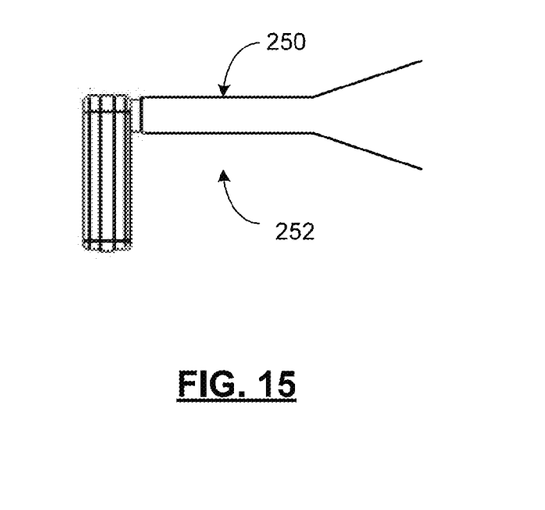
FIGS. 15 and 16 are side views of an embodiment of an end of a dental ultrasonography probe in accordance with the present invention.
Figure 16:
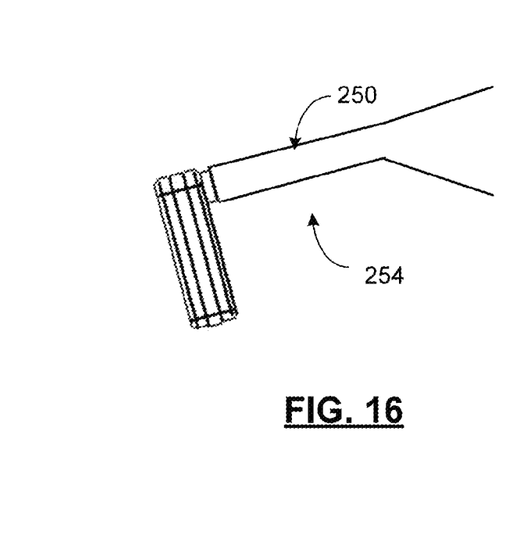

FIGS. 15 and 16 are side views of an embodiment of an end of a dental ultrasonography probe in accordance with the present invention. In particular an alternative end for dental ultrasonography probes 100, 175, 220, 230 or 240 is shown that includes an arm 250. As shown, the arm 250 is bendable between two different positions 252 and 254, again to provide greater flexibility in the positioning and orientation of the probe and the probe tip.

Figure 17:
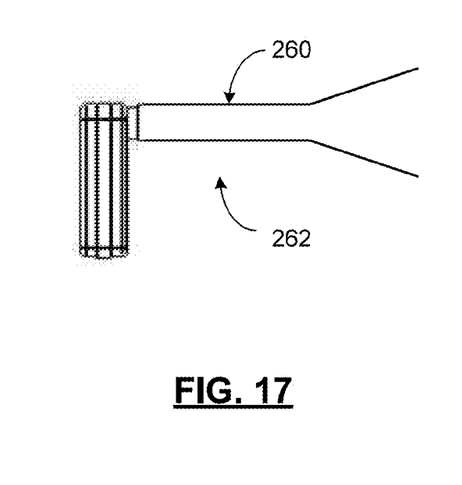
FIGS. 17 and 18 are side views of an embodiment of an end of a dental ultrasonography probe in accordance with the present invention.
Figure 18:
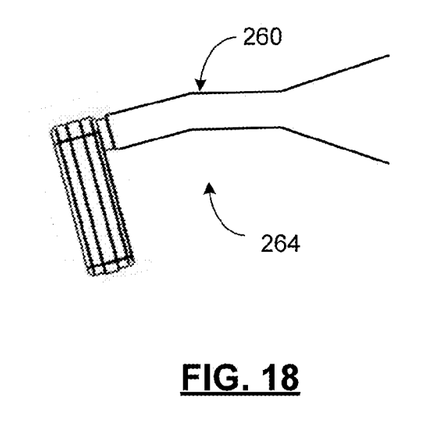

FIGS. 17 and 18 are side views of an embodiment of an end of a dental ultrasonography probe in accordance with the present invention. In particular an alternative end for dental ultrasonography probes 100, 175, 220, 230 or 240 is shown that includes an arm 260. As shown, the arm 260 is bendable between two different positions 262 and 264, again to provide greater flexibility in the positioning and orientation of the probe and the probe tip.

Figure 19:
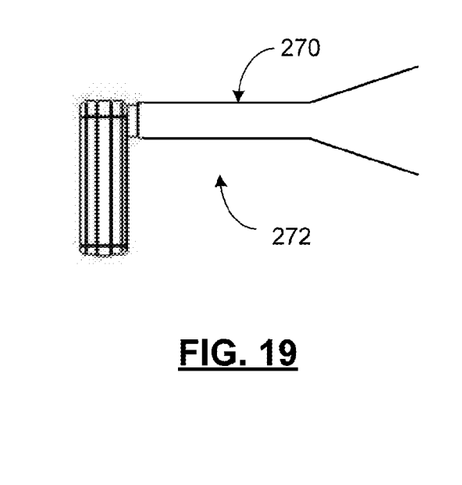
FIGS. 19 and 20 are side views of an embodiment of an end of a dental ultrasonography probe in accordance with the present invention.
Figure 20:
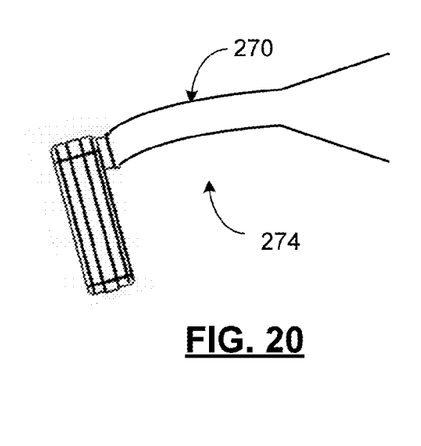

FIGS. 19 and 20 are side views of an embodiment of an end of a dental ultrasonography probe in accordance with the present invention. In particular an alternative end for dental ultrasonography probes 100, 175, 220, 230 or 240 is shown that includes an arm 270. As shown, the arm 270 is flexibly bendable between two different positions 272 and 274, again to provide greater flexibility in the positioning and orientation of the probe and the probe tip.

Figure 21:
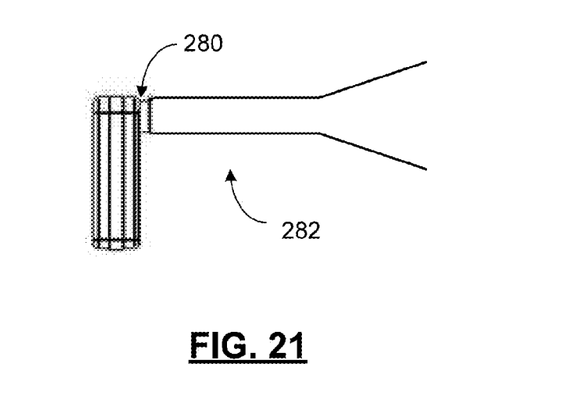
FIGS. 21 and 22 are side views of an embodiment of an end of a dental ultrasonography probe in accordance with the present invention.
Figure 22:
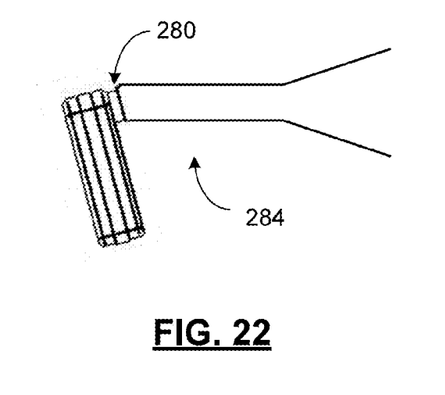

FIGS. 21 and 22 are side views of an embodiment of an end of a dental ultrasonography probe in accordance with the present invention. In particular an alternative end for dental ultrasonography probes 100, 175, 220, 230 or 240 is shown that includes an joint 280. As shown, the joint 280 is adjustable between two different positions 282 and 284, again to provide greater flexibility in the positioning and orientation of the probe and the probe tip.

Figure 23:
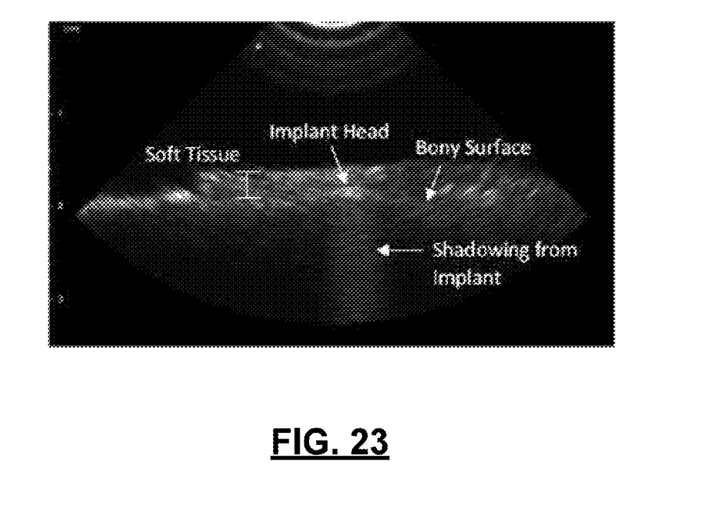
FIGS. 23 and 24 are screen displays of an embodiment of a processing display device in accordance with the present invention.
Figure 24:
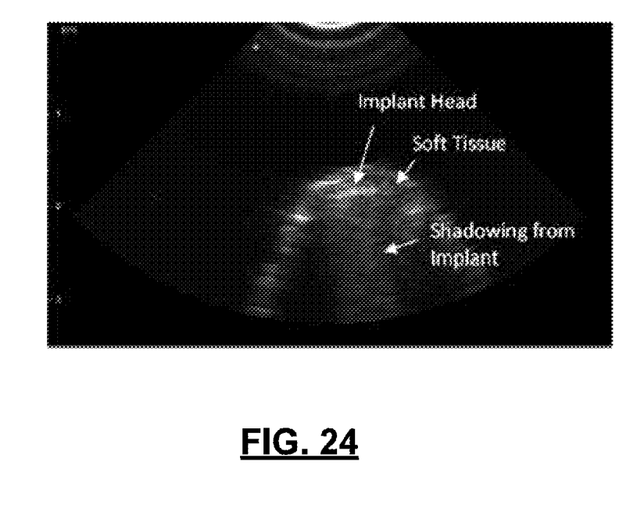

FIGS. 23 and 24 are screen displays of an embodiment of a processing display device in accordance with the present invention. As discussed in conjunction with FIG. 1, an ultrasound sector scanning transducer, ultrasonic array or other ultrasonic transducer is used in conjunction with a dental ultrasonography system 200 for imaging of the human jaw through the gums and in particular for detection or imaging of structures in or near the mouth. FIGS. 23 and 24 are screen displays of a display device 122 used in conjunction with such a system. Imaging data is displayed that aides the user in the manual detection of dental implants, the mental foramen, dehiscences, other bony defects and contours. The imaging can further include soft tissue thickness measurements such as measurements of the thickness of gum tissue, lips, cheeks and other soft tissues in or near the mouth.

In the particular images shown, the user can manually identify, locate and measure regions of interest such as soft tissue, and a bony surface. In addition, the user can identify, locate and measure implants based on the position of a bright implant head and a comet tail artifact that includes shadowing from the remaining implant body.

As discussed in conjunction with FIG. 2, the memory 118 can store a plurality of templates, such as exemplars of various structures to be detected such as soft tissues, dental implants, unerupted teeth, fixation screws, or other metallic objects, the mental foramen, dehiscences or fenestrations over teeth or implants, inherited defects to the craniofacial bones, such as a cleft palate or other defects, acquired defects, such as a gunshot or other traumatic damage are to the craniofacial bones, stones, in salivary ducts or glands, and other bony defects in the region of the teeth, jaw, checks, lips or other areas in or near the mouth. In a particular embodiment, templates are included for recognition of dental implants based on the identification and location of implant head and/or comet-tail shadowing from the implant body included in the ultrasonic imaging.

The ultrasonography application includes a pattern recognition algorithm that compares the ultrasonic receive data and/or ultrasonic image data to the exemplars. In particular, the pattern recognition algorithm operates to automatically detect and identify to the user soft tissues, dental implants, the mental foramen, dehiscences, and other bony defects in the ultrasonic images when the ultrasonic receive data and/or ultrasonic image data to a corresponding one of the plurality of exemplars. As shown in FIGS. 23, and 24, automatically identified features can be named, indicated and overlaid on the display.

Further, different colors can be used to display different structures that have been identified or detected to automatically locate and measure these structures and further to aid the user in visualizing the placement, size, shape and orientation of these structures in the patient's mouth.

FIGS. 25-30 are screen displays of an embodiment of a processing display device in accordance with the present invention. Screen displays 300, 302, 304, 306, 308 and 310 are further examples presented by display device 122 used in conjunction with dental ultrasonography system 200. In this embodiment, each display includes a top portion with simple ultrasonic imaging data. In a bottom portion of each display, an enhanced image is generated by processing the image data, that presents schematic representations of the features and artifacts identified in the image along with the relative position, size and intensity. In an embodiment of the present invention, once a particular object is recognized, based for instance on a recognition exemplar or template, a schematic figure based on the exemplar or template is presented in the bottom portion of the screen in a position, orientation and relative size to the recognized object. This further aids the user in reading the imaging results based on the objects that were automatically identified. As shown however, the imaging data itself is also presented on each screen to show the user the basis of the automatic identification and also to give the user the ability to possibly identify additional objects or features that may have been missed by the automatic identification.

Figure 25:
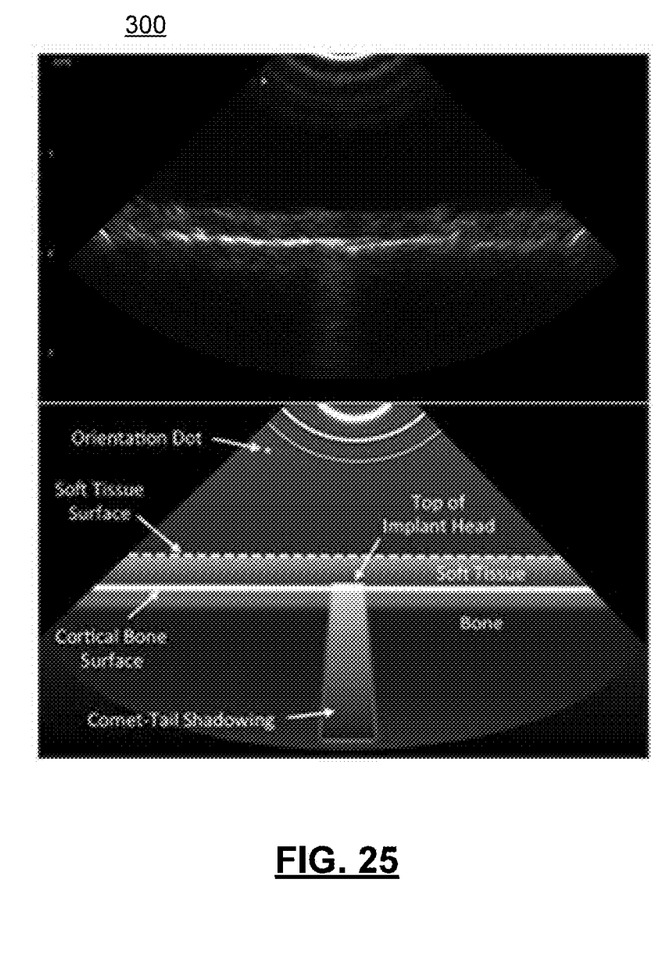
FIGS. 25-30 are screen displays of an embodiment of a processing display device in accordance with the present invention.
Figure 26:
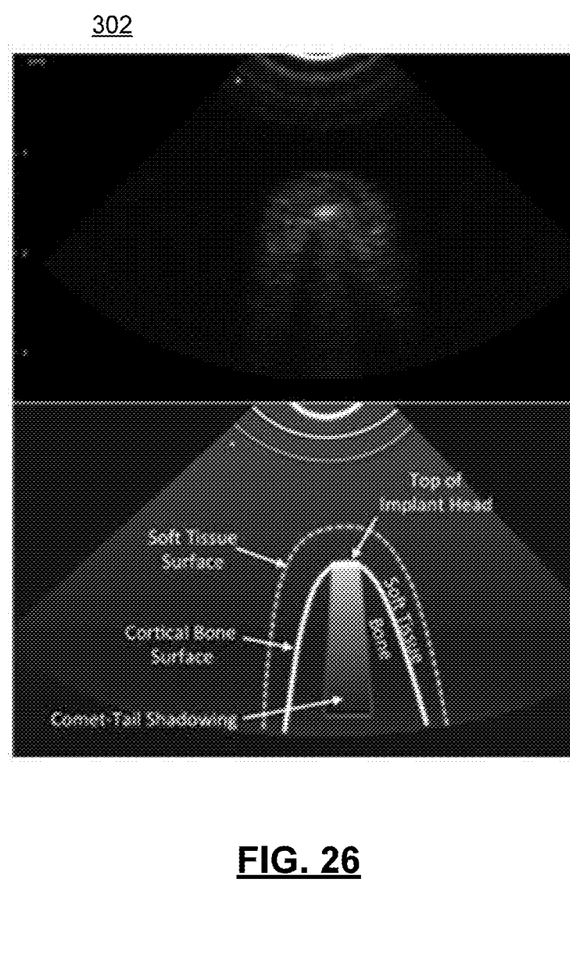
Figure 27:
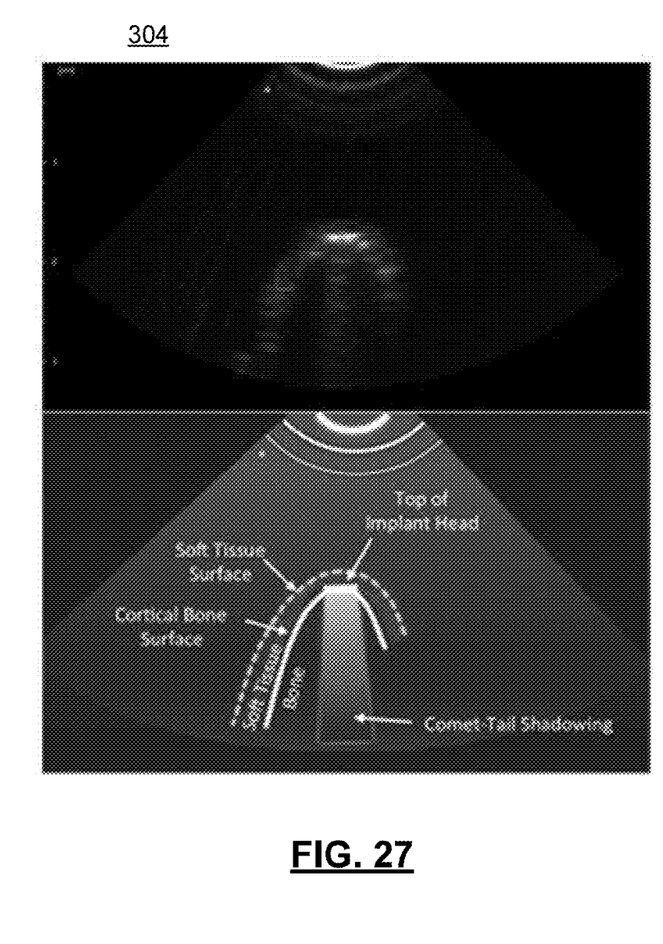
Figure 28:
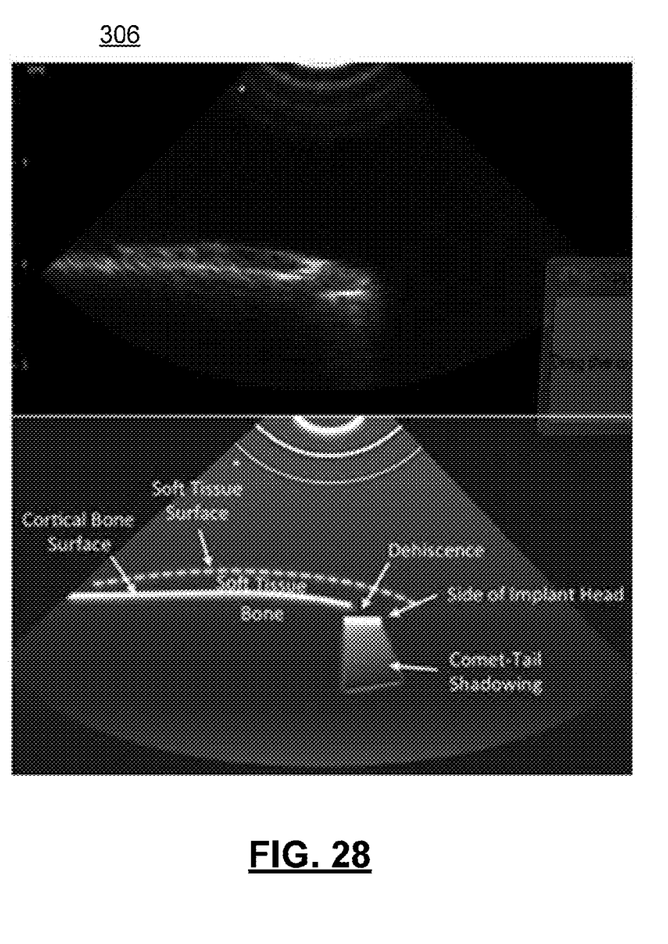
Figure 29:
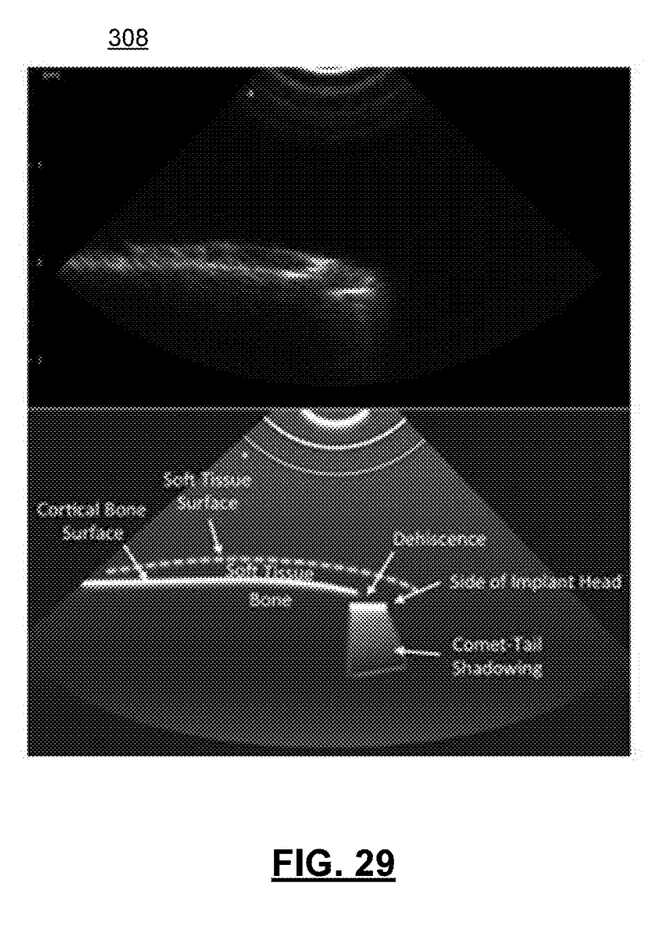
Figure 30:
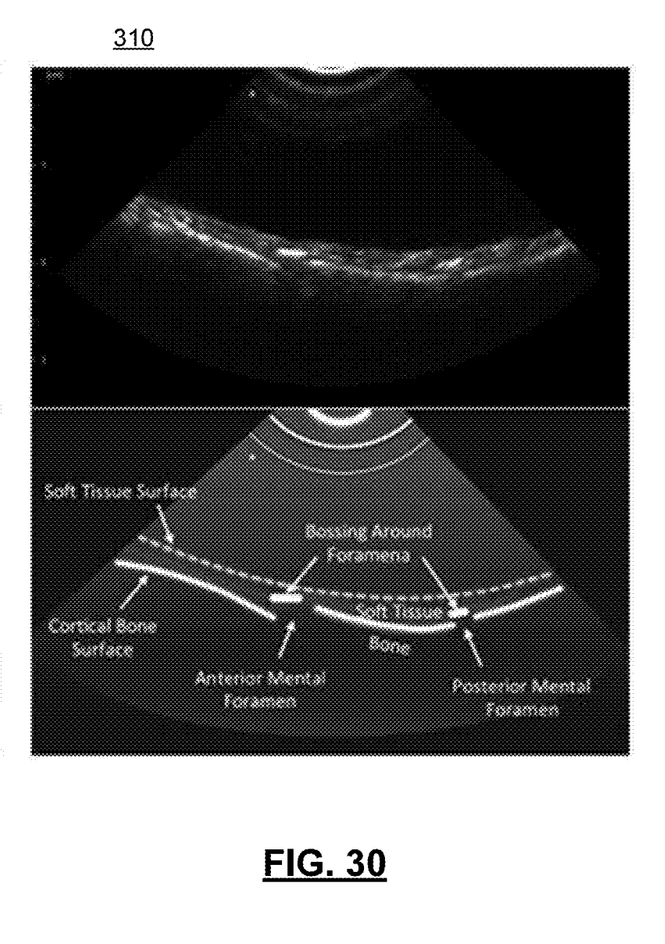

FIG. 25 presents a screen display 300 in response to ultrasonic imaging of implant placement in edentulous ridges (IE), with a view along the ridge crest. The bony ridge, implant head, and soft tissue are visible. FIG. 26 presents a screen display 302 in response to ultrasonic imaging of implant placement in edentulous ridges (IE), view across ridge crest. The bony ridge, implant head, and soft tissue are visible. FIG. 27 presents a screen display 304 in response to ultrasonic imaging of a single tooth replacement implant placement (IS) simulated by replacement of the lower left central incisor. The implant head, bony ridge and soft tissue are visible. FIG. 28 presents a screen display 306 in response to ultrasonic imaging of implant with a buccal dehiscence (ID), buccal view, ridge crest to right. Soft tissue overlies the buccal cortical plate and the dehiscence. The buccal cortical plate stops at the dehiscence. The floor of the dehiscence is seen as a very bright line from the implant head and exposed threads. FIG. 29 presents a screen display 308 in response to ultrasonic imaging of an incisor tooth with a buccal dehiscence (TD), buccal view, tooth crown to right. Soft tissue overlies the buccal cortical plate and the dehiscence. The buccal cortical plate gets duller at the dehiscence. The floor of the dehiscence is seen as a very bright line from root dentin. The root dentin is continuous with coronal enamel. FIG. 30 presents a screen display 310 in response to ultrasonic imaging of 2 major mental foramina (MF). This porcine jaw had 2 major mental foramina. Some bossing can be seen around the major foramina.

In each of the examples shown, various soft tissue surfaces and soft tissue regions, visible in the ultrasonic images are manually or automatically identified and indicated schematically in the bottom portion of the screen. Similarly, bone surfaces were clearly visible below the soft tissue, being further from the probe. The bone surfaces were brighter than the soft tissue surfaces; this can be ascribed to bone's large characteristic acoustic impedance relative to those of soft tissue, resulting in higher acoustic reflectivity. The areas below the bony surfaces are dark, because the dense reflective cortical plates reflected most of the acoustic energy back to the probe. The bone surface and regions of bone are manually or automatically identified and indicated schematically in the bottom portion of the screen.

As shown in screen displays 300, 302, 304, 306, 308, implants can be located when scanning along or across ridges. Implants are characterized in imaging data by a bright white reflective "cap" from the implant cover screw and head. The high reflectivity of the implants is ascribed to their high acoustic impedance relative to both bone and to soft tissue, as well as to their smoother reflective specular surfaces. Long grey shadows, known as "comet-tail artifacts", fall beneath the implant heads. This grey shadowing was the most consistent part of the implants' acoustic signatures and can be used in the automatic identification of these artifacts as previously described.

As shown in screen displays 306 and 308, implant dehiscences can be found, based on a very bright signal from titanium where a less bright signal from overlying cortical bone would normally have been expected. In these examples, the acoustic signature of a dehiscence was found to include two offset lines, with the upper line corresponding to the intact bone surface adjacent to the defect and the lower brighter line corresponding to the smooth side of the implant head on the wall of the dehiscence. The smooth implant heads are continuous with the less reflective roughened and threaded implant body surfaces. Because titanium is more reflective than bone, titanium surfaces appear as brighter lines than the bone surfaces. Because the buccal sides of the implants are further from the probe than the buccal cortical plate, they appeared below the buccal plate on the ultrasound images. The distance between the bone surface and the implant surface is indicative of the depth of the dehiscence.

Tooth dehiscences can be identified by finding a bright signal from dentin where a less bright signal from overlying cortical bone would normally be expected. In the example of FIG. 29, the acoustic signature of a dehiscence includes two offset lines, with the upper line corresponding to the intact bone surface adjacent to the defect and the lower line corresponding to the dentinal root surface on the wall of the dehiscence. The root surfaces in this case are contiguous with coronal enamel surfaces. Because both dentin and enamel are both more reflective than bone, their surfaces appear as brighter lines than those of adjacent buccal bone surfaces. Because both dentin and enamel are further from the probe than the buccal plate, they appear below the buccal plate on the images. The distance between the bone surface and the root surface is indicative of the depth of the dehiscence.

Mental foramina can be imaged based on their acoustic signatures which typically include one or more of several features, as shown in FIG. 30. First, a break in the cortical bone is evident. Second, the adjacent cortex can be shaped somewhat like an asymmetric funnel, depending upon the angle at which the nerve exited the bone. Third, dense bossing adjacent to the foramen can stand out as an especially bright short line directly above the foramen itself. This bossing appeared brighter because it is composed of denser more reflective cortical bone; it appeared above the foramen, because it is closer to the probe.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output (s), etc., to perform one or more its corresponding functions and may further include inferred coupling to one or more other items. As may still further be used herein, the term "associated with", includes direct and/or indirect coupling of separate items and/or one item being embedded within another item.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present invention has been described in conjunction with various illustrative embodiments that include many optional functions and features. It will be apparent to those skilled in the art that the disclosed invention may be modified in numerous ways, the functions and features of these embodiments can be combined in other embodiments not expressly shown, and may assume many embodiments other than the preferred forms specifically set out and described above. Accordingly, it is intended by the appended claims to cover all modifications of the invention which fall within the true spirit and scope of the invention.

What is claimed is:

1. A dental ultrasonography system comprising:
a dental ultrasonography probe that includes a scanning ultrasonography transducer that generates a narrow beam ultrasonic transmission signal over a sequence of beam angles, that receives an ultrasonic return signal, and that generates a receive signal in response to the ultrasonic return signal, wherein the scanning ultrasonography transducer includes a piezoelectric element to produce the sequence of beam angles, said sequence of beam angles and said receive signal coupled to a processing device which forms an image;
where said processing device receives the receive signal to automatically detect at least one dental feature used in dental implant therapy;
said automatic detection performing a comparison of said receive signal to a plurality of exemplars stored in a memory, said exemplars including at least one of: soft tissue, a dental implant, an unerupted tooth, a fixation screw, a metallic object, mental foramen, a dehiscence over a tooth, a fenestration over a tooth, a dehiscence over a dental implant, a fenestration over a dental implant, an inherited defect to a craniofacial bone, an acquired defect to a craniofacial bone, a stone in a salivary duct, a stone in a gland, presence of a foreign body in soft tissue, or gingiva; at least one said exemplar having an associated image overlay;
where, upon a matching comparison of said receive signal to at least one of said exemplars, said processing device displays said image overlay associated with said matching exemplar positioned adjacent to said matching comparison in said image.

2. The dental ultrasonography system of claim 1 where, upon said matching comparison, said image overlay indicates at least one of: text, a numerical measurement, indicating the matching exemplar, an outline of said matching exemplar, or the extents of said matching exemplar.

3. The dental ultrasonography system of claim 1 where at least one of said exemplars is an implant detected by the finding of a bright white reflective cap followed by a grey shadowing below said reflective cap.

4. The dental ultrasonography system of claim 3 where said associated image overlay for said implant is at least one: of text indicating an implant head, a numerical measurement, an outline of said matching exemplar, or the identification of the extent of said implant.

5. The dental ultrasonography system of claim 1 where at least one of said exemplars is a soft tissue surface.

6. The dental ultrasonography system of claim 1 where at least one of said exemplars is a very bright signal surrounded by less bright signal.

7. The dental ultrasonography probe of claim 6 where said associated image overlay for said very bright signal surrounded by less bright signal as two offset lines.

8. The dental ultrasonography system of claim 6 where said associated image overlay for said very bright signal surrounded by less bright signal is at least one of: text indicating a dehiscence, a numerical measurement, the indication of an outline or extent of a dehiscence, the depth of a dehiscence determined by the separation of said very bright signal from said less bright signal, or a measurement of the extent of a dehiscence.

9. The dental ultrasonography system of claim 1 where at least one of said exemplars is bright signal where less bright signal of surrounding cortical bone is expected, said exemplar including two offset lines.

10. The dental ultrasonography system of claim 9 where said associated image overlay is at least one of: text identifying a dehiscence, a numerical measurement, an indication of intact bone surface for the upper of two said offset lines, a dentinal root surface on the lower of said two offset lines, the indication of the extents of a dehiscence, or a measurement of the extent of a dehiscence.

11. The dental ultrasonography system of claim 1 where at least one of said exemplars is a bright signal followed by less bright signal, said associated image overlay indicating buccal bone adjacent to said bright signal, said associated image overlay also indicating dentin or enamel adjacent to said less bright signal.

12. The dental ultrasonography system of claim 11 where said associated image overlay also includes at least one of: text indicating dentin, text indicating enamel, text indicating buccal bone, a numerical measurement, or a measurement indicating the distance between said bright signal and said less bright signal.

13. The dental ultrasonography system of claim 1 wherein the processing device is included in a personal computer and wherein the dental ultrasonography system further comprises:
   a computer interface for attachably coupling the dental ultrasonography probe to the personal computer.

14. The dental ultrasonography system of claim 1 where said exemplar includes the identification of cortical bone, identification of a break in said cortical bone, identification of an adjacent cortex shaped like an asymmetric funnel, and where said associated overlay image includes at least one of: text indicating mental foramina, the outline or extents of mental foramina, or a measurement of the extents of mental foramina.

15. The dental ultrasonography system of claim 1 where said scanning ultrasonography transducer is at least one of a sector scanning transducer or an ultrasonic array.

16. The dental ultrasonography system of claim 1 where said scanning ultrasonography transducer is at least one of a phased ultrasound array, a linear ultrasound array, an annular ultrasound array, a two-dimensional array, a mechanical rotating array, or a sector scanner.

17. The dental ultrasonography system of claim 1 where said scanning ultrasonography transducer is a piezoelectric material including at least one of a crystal, a single crystal, a ceramic, a piezoelectric composite, a sol-gel, a polymer, or a capacitive micromachined ultrasound transducer (CMUT).

18. A method for automatic detection of dental features in a system;
   the system comprising a dental ultrasonography probe that includes a scanning ultrasonography transducer that generates a narrow beam ultrasonic transmission signal over a sequence of beam angles, that receives an ultrasonic return signal, and that generates a receive signal in response to the ultrasonic return signal, wherein the scanning ultrasonography transducer includes a piezoelectric element to produce the sequence of beam angles, said sequence of beam angles and said receive signal coupled to a processing device which forms an image;
   said process having the steps of:
   performing a comparison of said receive signal to a plurality of exemplars stored in a memory, said exemplars including at least one of: soft tissue, a dental implant, an unerupted tooth, a fixation screw, a metallic object, mental foramen, a dehiscence over a tooth, a fenestration over a tooth, a dehiscence over a dental implant, a fenestration over a dental implant, an inherited defect to a craniofacial bone, an acquired defect to a craniofacial bone, a stone in a salivary duct, a stone in a gland, presence of a foreign body in soft tissue, or gingiva;
   where, upon a matching comparison of said receive signal to at least one of said exemplars, said processing device displays an image overlay associated with said matching exemplar, said image overlay positioned adjacent to said matching exemplar in said image.

19. The process of claim 18 where said image overlay indicates at least one of: text associated with said matching exemplar, the extent of said matching exemplar, a distance measurement associated with said matching exemplar, or an outline of said matching exemplar.

20. The process of claim 18 where said text identifies said matching exemplar.

* * * * *